(12) United States Patent
Boyer et al.

(10) Patent No.: US 11,525,382 B2
(45) Date of Patent: Dec. 13, 2022

(54) METHOD FOR ANALYSING THE OPERATION OF AN ANTI-POLLUTION SYSTEM FOR A MOTOR VEHICLE

(71) Applicants: CONTINENTAL AUTOMOTIVE FRANCE, Toulouse (FR); CONTINENTAL AUTOMOTIVE GmbH, Hannover (DE)

(72) Inventors: Jean-Luc Boyer, Tournefeuille (FR); Ludovic Rocher, Balma (FR)

(73) Assignees: CONTINENTAL AUTOMOTIVE FRANCE, Toulouse (FR); CONTINENTAL AUTOMOTIVE GMBH, Hannover (DE)

( * ) Notice: Subject to any disclaimer, the term of this patent is extended or adjusted under 35 U.S.C. 154(b) by 231 days.

(21) Appl. No.: 16/633,609

(22) PCT Filed: Jul. 16, 2018

(86) PCT No.: PCT/FR2018/051798
§ 371 (c)(1),
(2) Date: Jan. 24, 2020

(87) PCT Pub. No.: WO2019/020900
PCT Pub. Date: Jan. 31, 2019

(65) Prior Publication Data
US 2020/0208560 A1    Jul. 2, 2020

(30) Foreign Application Priority Data

Jul. 25, 2017 (FR) .................................. 1757068

(51) Int. Cl.
*F01N 11/00* (2006.01)
*F01N 9/00* (2006.01)
*G01N 33/00* (2006.01)

(52) U.S. Cl.
CPC .............. *F01N 9/007* (2013.01); *F01N 11/00* (2013.01); *G01N 33/0062* (2013.01);
(Continued)

(58) Field of Classification Search
CPC .. F01N 9/007; F01N 11/00; F01N 2900/0412; F01N 2900/08; F01N 2900/10;
(Continued)

(56) References Cited

U.S. PATENT DOCUMENTS 5,829,248 A    11/1998   Clifton
5,941,918 A *  8/1999    Blosser ................. F01N 13/008
                                                          701/31.7
(Continued)

FOREIGN PATENT DOCUMENTS

CN    103089388 A    5/2013
CN    103256109 A    8/2013
(Continued)

OTHER PUBLICATIONS

Office Action issued in Chinese Patent Application No. 201880062022.7 dated Apr. 30, 2021.
(Continued)

*Primary Examiner* — Matthew T Largi
(74) *Attorney, Agent, or Firm* — Nixon & Vanderhye

(57) ABSTRACT

The present invention relates to a method for analysing the operation of an anti-pollution system for a motor vehicle (1) with an internal combustion engine, said vehicle (1) comprising at least one sensor for measuring (110) a parameter of the vehicle (1) and an analysis computation means (140) directly connected to said measuring sensor (110), said analysis computation means (140) comprising a memory area, said method being characterised in that it comprises a step for using the measuring sensor (110) to measure at least one parameter of the vehicle (1), a step for using the
(Continued)

measuring sensor (110) to transmit at least one digital datum representative of the measured value of the parameter to the analysis computation means (140) and a step for using the analysis computation means (140) to compare said digital datum with a predetermined range of values representative of an operation of the anti-pollution system according to a predetermined standard.

19 Claims, 2 Drawing Sheets

(52) U.S. Cl.
CPC .. *F01N 2900/0412* (2013.01); *F01N 2900/08* (2013.01); *F01N 2900/10* (2013.01); *F01N 2900/12* (2013.01); *G01N 2033/0068* (2013.01)

(58) Field of Classification Search
CPC ............ F01N 2900/12; G01N 33/0062; G01N 2033/0068
See application file for complete search history.

(56) References Cited

U.S. PATENT DOCUMENTS

| | | | |
|---|---|---|---|
| 5,941,928 A | 8/1999 | Naber et al. | |
| 7,117,079 B2 | 10/2006 | Streichsbier et al. | |
| 8,332,121 B2 | 12/2012 | Adams | |
| 8,478,501 B1 | 7/2013 | Adams | |
| 8,495,860 B2 | 7/2013 | Gresens | |
| 8,762,791 B2 | 6/2014 | Nakamura et al. | |
| 9,068,492 B2 | 6/2015 | Bogema et al. | |
| 9,513,191 B2 | 12/2016 | Schankula et al. | |
| 11,161,844 B2 * | 11/2021 | Chappie | C07D 471/04 |
| 2007/0035384 A1 * | 2/2007 | Belcher | H04M 1/67 340/425.5 |
| 2007/0129878 A1 | 6/2007 | Pepper | |
| 2011/0231055 A1 * | 9/2011 | Knight | G07C 5/008 701/31.4 |
| 2012/0297235 A1 | 11/2012 | Nakamura et al. | |
| 2013/0024066 A1 | 1/2013 | Geilen et al. | |
| 2013/0116881 A1 | 5/2013 | Bogema et al. | |
| 2014/0277904 A1 | 9/2014 | Schankula et al. | |
| 2015/0379788 A1 * | 12/2015 | Raynal | G07C 5/085 701/32.7 |
| 2016/0110935 A1 | 4/2016 | Kwak | |
| 2018/0158145 A1 * | 6/2018 | Weigel | G06Q 40/06 |
| 2018/0315257 A1 * | 11/2018 | Boyer | G07C 5/04 |
| 2020/0036310 A1 * | 1/2020 | Sarder | H02J 7/1415 |

FOREIGN PATENT DOCUMENTS

| | | |
|---|---|---|
| CN | 105604664 A | 5/2016 |
| CN | 105675101 A | 6/2016 |
| DE | 10 2008 018 028 A1 | 11/2008 |
| EP | 2530550 A1 | 12/2012 |
| JP | 2007-002700 A | 1/2007 |
| WO | 03/067350 A2 | 8/2003 |
| WO | 2011/057359 A1 | 5/2011 |
| WO | 2012/016155 A1 | 2/2012 |
| WO | 2012/167810 A1 | 12/2012 |

OTHER PUBLICATIONS

Examination Report issued in IN Patent Application No. 202017002424 dated Sep. 9, 2021, with English translation provided.
International Search Report, dated Nov. 7, 2018, from corresponding PCT application No. PCT/FR2018/051798.

* cited by examiner

METHOD FOR ANALYSING THE OPERATION OF AN ANTI-POLLUTION SYSTEM FOR A MOTOR VEHICLE

BACKGROUND OF THE INVENTION

Field of the Invention

The invention relates to the field of motor vehicle diagnostics and pertains more particularly to a method for analyzing the functioning of an anti-pollution system of a motor vehicle.

The present invention aims notably to prevent any tampering with the anti-pollution system that would result in modifying the comparison of measurements of pollutant emissions from the engine against levels measured in type-approval or diagnostics testing of the vehicle.

Description of the Related Art

In a motor vehicle with a combustion engine, a mixture of gasoline and air combusts to generate the mechanical energy that enables the vehicle to move. Such combustion emits residual gases that may have an environmental impact, such as, for example, nitrous oxides ($NO_X$) or carbon dioxide ($CO_2$).

Nowadays, there are numerous standards aimed at policing these pollutant emissions. In particular, it is known to carry out diagnostics at the time of the type-approval testing of the vehicle as it rolls off the assembly line, or during maintenance testing on the vehicle with a view to certifying that it complies with the standards in force.

For the purpose of reducing pollutant gas emission levels, it is also known to install an anti-pollution system in the vehicle with a view to limiting pollutant gas release. During the life of the vehicle, however, the anti-pollution system may suffer wear and become degraded, resulting in a drop in its efficiency, which may increase releases of certain pollutant gases and lead to pollutant gas emission levels that exceed the standards in force. It is thus known to fit sensors into the vehicle in order to verify that the anti-pollution system is functioning properly. These sensors may, for example, be temperature sensors, gas measurement sensors, etc.

U.S. Pat. No. 9,068,492 discloses an onboard computation means that detects the deterioration of an anti-pollution system of a motor vehicle. This computation means is connected to the sensors with a view to detecting such wear. The sensors of the anti-pollution system send analog signals to the computation means, which filters them and linearizes them so that they can be used in the form of physical values. The computation means then checks that these values correspond to representative thresholds for normal functioning of the anti-pollution system, i.e. that the anti-pollution system complies with the anti-pollution standards in force.

Nevertheless, it has been observed that it was possible to modify the anti-pollution system so as to falsify the signals used for diagnostics. In this case, these signals can fall within the limits imposed by the standard despite the fact that the pollutant gas release levels are in fact outside these limits. In this case, although the vehicle does not comply with anti-pollution standards, the computation means does not diagnose any abnormal functioning of the anti-pollution system.

The analog signals generated by the sensors may be falsified by adding electronic components between the sensors and the computation means such as to deceive the computation means when diagnostics are being carried out or with a view to increasing the power of the engine to the detriment of pollutant gas releases when the computation means is used to command the injection of fuel into the engine of the vehicle. It is also known to falsify the processing of the signals by the computation means by modifying the calibration used by said computation means to perform the diagnostics, notably by re-programming the computation means in order to modify certain coefficients used in the calculation formulae for converting the electrical signals from the sensors into physical values.

The need therefore exists for a solution that makes it possible to remedy these drawbacks at least in part.

SUMMARY OF THE INVENTION

The present invention aims to propose a simple, reliable and effective solution for the analysis of the functioning of an anti-pollution system while limiting the risk of falsification of the analysis.

To that end, the subject of the invention is a method for analyzing the functioning of an anti-pollution system of a motor vehicle with a combustion engine, said vehicle comprising at least one sensor for measurement of a parameter of the vehicle and an analytical computation means connected to said measurement sensor, said analytical computation means comprising a memory zone.

Said method is noteworthy in that it comprises a step of measurement by the analytical sensor of at least one parameter of the vehicle, a step of generation by the analytical sensor of at least one numerical data item representative of the measured value of the parameter, a step of transmission by the analytical sensor of said numerical data item to the analytical computation means, effected over a direct communication link between the sensor and the analytical computation means, a step of comparison by the analytical computation means of said numerical data item against a predetermined range of values representative of a functioning of the anti-pollution system in accordance with a predetermined standard, and a step of storage of the numerical data item in the memory zone only when said numerical data item is not included in said range of values such as to detect an abnormal functioning of the anti-pollution system.

By virtue of the method according to the invention, the risk of the signals being modified with a view to falsifying the analysis of the anti-pollution system is reduced, or even eliminated, owing to the transmission to the analytical computation means of the "raw" numerical data generated by the sensor. The numerical data representative of the measured parameter are called "raw data" because they have not undergone any treatment, i.e. no conversion, notably into a physical value, which makes it possible to limit, or even to eliminate, the risk of falsification. This further allows real-time analysis of the anti-pollution system. More precisely, the comparison of the measured data item against a range of values makes it possible to detect a deterioration in the anti-pollution system when the value of the numerical data item is below the lower boundary of the range of values and an improved status of the anti-pollution system over that which is measured when the value of the numerical data item is above the upper boundary of the range of values. This latter case, which cannot be detected with prior art solutions, is representative of a falsification of the data item and can thus be readily detected with the method according to the invention. Advantageously, when a measured data item is outside the range of values, the data item is recorded so as to enable an operator subsequently, for example at the time of an inspection, to detect an abnormal functioning of the anti-pollution system.

In connection with the transmission by the sensor of the numerical data item to the analytical computation means, which is effected over a direct communication link between the sensor and the analytical computation means: "Direct" is understood to mean that the measurement sensor and the analytical computation means are directly connected with no intermediate component and with no software processing between the measurement sensor and the analytical computation means.

Preferably, the numerical data item is a data item in hexadecimal format, so as to efficiently prevent the falsification of said data item when it is sent by the measurement sensor to the analytical computation means.

Advantageously, the method comprises a step of acquiring the numerical data item stored in the memory zone so as to enable an operator to analyze the functioning of the anti-pollution system.

Preferably, again, the numerical data item stored is acquired by an analytical terminal connected to the vehicle. Thus, at the time of an analytical operation, an operator connects the terminal to the vehicle with a view to reading the numerical data item or data stored and to detecting any abnormal functioning of the anti-pollution system.

Advantageously, the parameter of the vehicle being measured at a functioning point of the vehicle, the predetermined range of values corresponds to said functioning point. Thus, the data item is compared empirically and therefore does not need to be processed in order to be analyzed.

Preferably, the method comprises a preliminary step of determination of at least one range of values at a functioning point of the vehicle, for example on a test bench or on a moving vehicle.

Preferably, the range of values is confirmed by calculation, using the laws of thermodynamics that characterize combustion in an engine. In other words, by virtue of the method according to the invention, compliance of the anti-pollution system with a standard may be checked by comparison against characterization values of the anti-pollution system obtained experimentally on the basis of actual measurements carried out on a vehicle fleet and supplemented with calculations based on the physical laws of combustion in the combustion engine.

Preferably, again, a functioning point of the vehicle is defined by the speed of rotation of the engine, the speed of the vehicle, the temperature of the engine and/or the temperature outside the vehicle, etc.

Advantageously, the method comprises a preliminary step of determination of at least two ranges of values, each range of values being determined for a different functioning point of the vehicle. Thus, for each functioning point of the vehicle, a table of values is determined such that it is possible to compare the data item measured at the corresponding functioning point.

The invention also relates to a vehicle comprising at least one sensor for measurement of at least one parameter of the vehicle and at least one analytical computation means connected to said sensor and comprising a memory zone, said vehicle being adapted such as to implement the method as described previously.

By virtue of the vehicle according to the invention, the risk of falsification of the data is limited, or even eliminated, the analytical computation means receiving raw numerical data from the sensor.

According to a feature of the invention, the sensor is connected electrically to the analytical computation means via a direct communication link so as to prevent any modification of the numerical data between the measurement sensor and the analytical computation means. "Direct communication link" is understood to mean a point-to-point electrical connection between the sensor and the analytical computation means.

According to a first embodiment of the invention, the analytical computation means is a dedicated computation means, which is otherwise said to be independent of any other computation means of the vehicle, notably the engine control computation means of the vehicle.

According to a second embodiment, the analytical computation means takes the form of a module, for example software, integrated into an engine control computation means of the vehicle.

Other features and advantages of the invention will become apparent from the following description, given with reference to the appended figures that are given by way of non-limiting example and in which identical references are given to similar objects.

DESCRIPTION OF THE PREFERRED EMBODIMENTS

Figure 1:
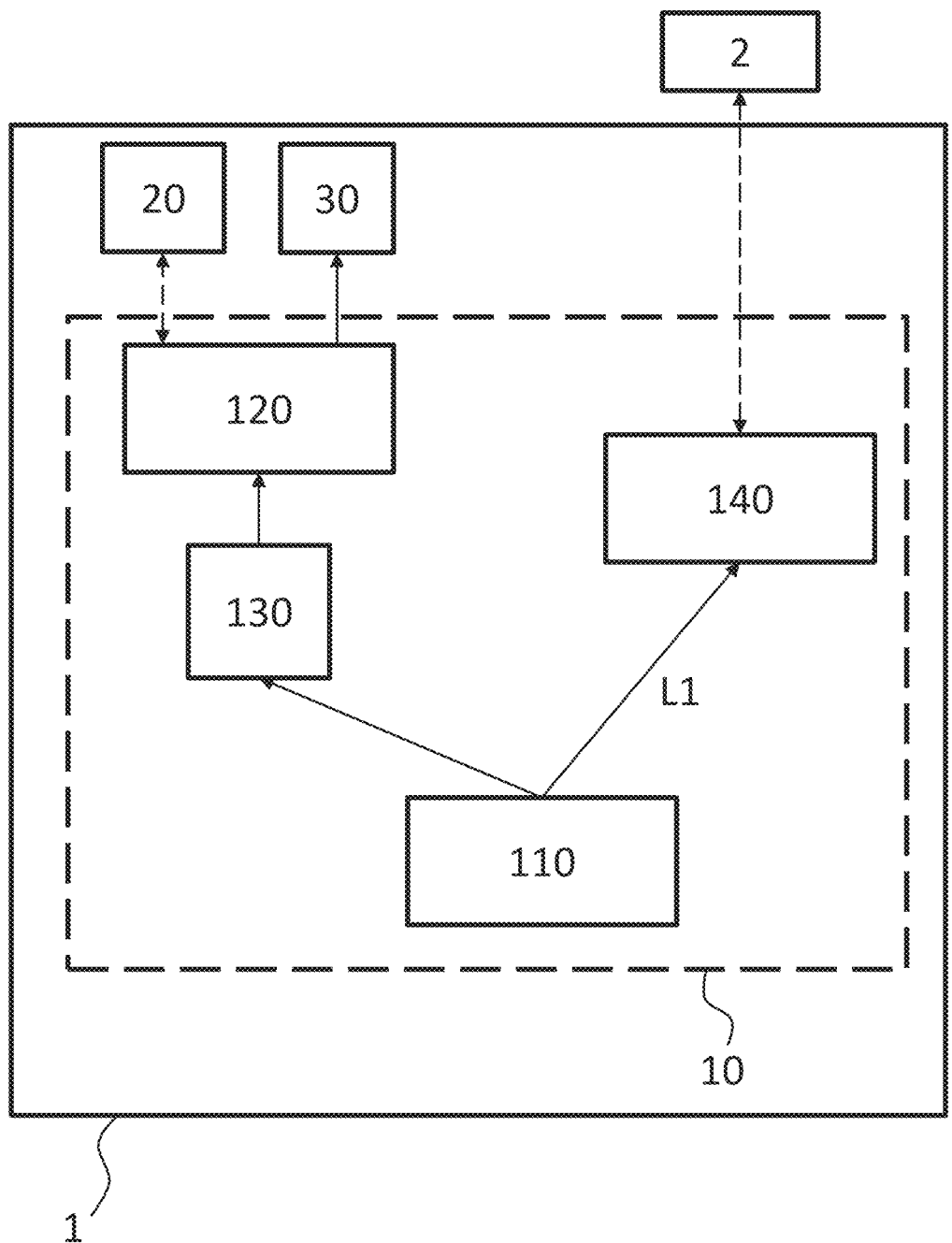
FIG. 1 schematically illustrates one embodiment of the analytical system according to the invention.

The invention will now be described with reference to FIG. 1. The invention is designed for vehicles, notably automobiles, with a view to analyzing the functioning of their anti-pollution system.

The vehicle 1 according to the invention comprises a combustion engine (not shown), an anti-pollution system (not shown) for the exhaust gases of the combustion engine, and a system 10 for analyzing the functioning of the anti-pollution system.

The engine comprises a plurality of cylinders each defining a combustion chamber into which a volume of fuel and a volume of air are introduced upon each cycle of the engine so as to combust the mixture thereof.

Each cylinder comprises a piston mounted in the combustion chamber. The piston is designed to be driven in translation by the combustion of the mixture in the combustion chamber. The pistons drive the rotation of a main shaft of the engine, also denoted 'engine flywheel', thus allowing the engine to convert the energy released by combustion into mechanical energy.

The combustion of such a mixture of fuel and air emits residual gases such as, for example, nitrous oxides ($NO_X$) or carbon dioxide ($CO_2$). Such residual gases may have an environmental impact. Thus, there are standards that aim to impose a maximum residual gas release threshold.

The purpose of the anti-pollution system is to limit the amount of residual gases released by the vehicle 1. To that end, the anti-pollution system comprises, in a known manner, an exhaust line adapted to guide the exhaust gases from the combustion chamber toward the exterior of the vehicle. The anti-pollution system comprises, notably, a catalytic converter, also denoted a "catalyzer", which is adapted to reduce the toxicity of the exhaust gases guided in the anti-pollution system. The catalytic converter comprises active elements adapted to react with the exhaust gases so as to convert the toxic elements of the exhaust gases. The functioning of such a catalytic converter being known, it will not be described in greater detail here.

The analytical system 10 is adapted such as to monitor the satisfactory functioning of the anti-pollution system. To that end, the analytical system 10 comprises at least one measurement sensor 110 connected, first, to a processing computation means 120 via processing means 130 and, second, to an analytical computation means 140 over a direct communication link L1.

The sensor 110 is adapted such as to measure at least one parameter representative of the functioning of the anti-pollution system. Such a sensor 110 may, for example, be a sensor for measurement of the temperature of the liquid coolant of the engine, a camshaft or crankshaft sensor adapted such as to determine the speed of rotation of the engine, a gearbox sensor adapted such as to determine the gear that is engaged, an accelerator pedal position sensor, a sensor for measurement of the amount of fuel injected, a sensor for measurement of at least one gas, such as oxygen, nitrous oxide $NO_x$, etc.

For the sake of clarity and simplification, an analytical system 10 is presented that comprises a single sensor 110, but it could, of course, comprise a plurality thereof, the analysis of the functioning of the anti-pollution system then being effected with the aid of the data measured by the sensors overall.

The sensor 110 is adapted such as to generate "raw" numerical data on the basis of the measurements of the parameter that are carried out and to send these numerical data, encoded in an electrical signal, to the processing computation means 120, via the processing means 130, and to the analytical computation means 140 over the direct communication link L1. Raw numerical data are thus understood to be the numerical data sent by the sensor 110.

Preferably, the raw numerical data are in hexadecimal format. The value of the raw numerical data may, for example, be between 00000 and 7FFFH for positive values of the parameter to be measured.

The processing means 130 are configured such as to filter and to linearize the electrical signal received from the sensor 110 so as to enable the processing computation means 120 to exploit the data thus processed. More precisely, the processing means 130 make it possible to convert each numerical data item into a physical value, for example a temperature value or an electric voltage value, which may be exploited by the processing computation means 120.

In this preferred example, the processing computation means 120 is adapted such as to send the processed data (i.e. the physical values of the parameters) to an engine control computation means 20 (denoted ECU, standing for Engine Control Unit). In a variant, it will be noted that the processing computation means 120 and the engine control computation means 20 could be implemented by one and the same physical entity of ECU type.

The engine control computation means 20 is adapted such as to command the injection of fuel and of air into the combustion engine, on the basis of the processed data, such as to limit gas and unburned-fuel release.

Preferably, the vehicle 1 also comprises an indicator 30 for signaling that there is a functioning problem in the anti-pollution system. The processing computation means 120 is adapted such as to send a signal to the indicator 30 when the processed data reveal an abnormal functioning of the anti-pollution system. The indicator 30 is thus adapted such as to emit a luminous signal to the driver of the vehicle 1 so as to inform the driver about a functioning problem of the anti-pollution system.

The analytical computation means 140 receives the raw numerical data directly from the sensor 110 over the direct communication link L1. In other words, no data-processing means is placed between the sensor 110 and the analytical computation means 140.

The analytical computation means 140 comprises a memory zone (not shown), in which are stored one or more predetermined ranges (or intervals) of values.

Preferably, the memory zone comprises a range of values for each functioning point of the combustion engine. For a given measurement sensor 110, each range of values is representative of a functioning of the anti-pollution system compliant with anti-pollution standards for a functioning point of the given engine.

A functioning point of the engine may, notably, be defined by a speed of rotation of the engine, a temperature of the engine, etc. Each range of values is determined in advance empirically, for example on a test bench or on a moving vehicle, which makes it possible to determine ranges of values of numerical data rather than physical values.

For example, when characterizing a plurality of vehicles 1, the minimum value and the maximum value measured by a sensor 110, for example an oxygen probe, when the engine has a specific status (for example, when the engine is cold, the oxygen probe is cold, first gear is engaged and a specific torque is required).

Moreover, each range of values may be validated by calculation based on physical laws, in particular the laws of thermodynamics, representative of the functioning of a combustion engine.

The analytical computation means 140 is adapted such as to compare a raw numerical data item received from the sensor 110 against one of the stored ranges of values so as to determine whether the functioning of the anti-pollution system is normal or abnormal.

More precisely, since each raw numerical data item may be associated with a functioning point of the engine, the analytical computation means 140 is adapted such as to compare a raw numerical data item received from the sensor 110, measured at a given functioning point of the engine, against the range of value corresponding to said functioning point, stored in the memory zone.

Thus, when a functioning point for which a range of values is stored is identified, if the raw numerical data item is within the range of values corresponding to the functioning point, the functioning of the anti-pollution system is deemed to comply with the functioning point of the corresponding engine.

Advantageously, a range of values being defined as an interval of values between a lower boundary and an upper boundary, the comparison of the raw data item against such a range of values makes it possible to detect not only when a numerical data item is below the lower boundary of the range but also when a numerical data item is above the upper boundary. When the numerical data item is below the lower boundary, it is inferred that the anti-pollution system has suffered a deterioration. On the other hand, when the numerical data item is above the upper boundary of the range, it is inferred that the numerical data item has been falsified. Indeed, a range of values is determined on the basis of pollution models that are physically possible so as to detect measurement values that reflect an abnormal and physically impossible improvement in the functioning of the anti-pollution system. Thus, comparison against a range of values makes it possible to detect not only a deterioration in the anti-pollution system (for example, after removal of a component from the vehicle) but also a falsification of the system (for example, when acquired items are altered in order to conceal pollution).

When the numerical data item is outside the range of values, it is stored in the memory zone of the analytical computation means 140. Preferably, the data item is stored with other information such as, for example, the date and time of the measurement of the data item, the functioning point of the engine at which the data item was measured, etc.

The analytical computation means 140 behaves as a black box for the analysis of the functioning of the anti-pollution system, because it is isolated and cannot be falsified. Alternately, the analytical computation means 140 and the engine control computation means 20 could be implemented in the form of one and the same physical entity, for example the analytical computation means 140 could take the form of an independent software module integrated into the engine control computation means 20 so as to preserve isolated functioning relative to the rest of the engine control computation means 20 and to limit the number of elements in the vehicle.

An analytical terminal 2 may be connected to the vehicle, for example by a diagnostics connection, also denoted "OBD connection", standing for On Board Diagnostics, with a view to performing diagnostics on the functioning of the anti-pollution system. Such an analytical terminal 2 is adapted such as to be connected to the analytical computation means 140 and to read the data stored in the memory zone thereof. Thus, an operator is able to analyze the system after the measurement by virtue of the storage of the data in the memory zone. The operator can also ascertain the functioning point at which abnormal functioning arose and the date on which it arose.

Figure 2:
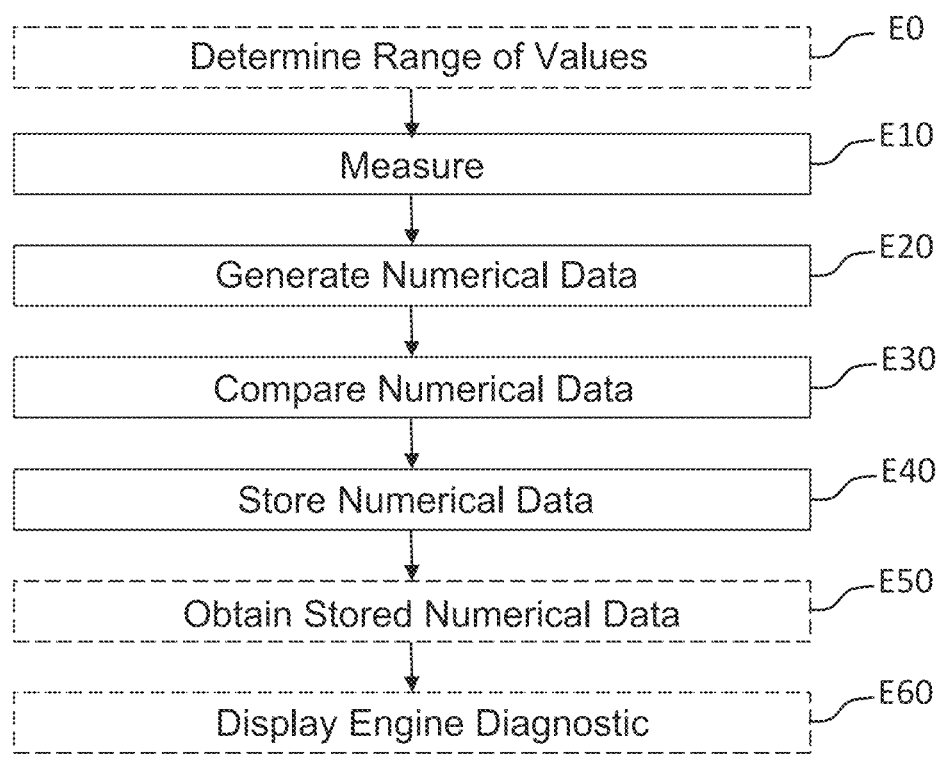
FIG. 2 schematically illustrates the implementation of the method according to the invention.

The method according to the invention and the analysis of the functioning of the anti-pollution system of a vehicle 1 will now be presented with reference to FIG. 2.

In a preliminary step E0, a range of values representative of normal functioning of the anti-pollution system is determined for each functioning point of the vehicle 1.

During the functioning of the vehicle 1, the sensor 110 measures a parameter of the vehicle 1 in a step E10.

Next, the sensor 110 generates, in a step E20, a numerical data item representative of the measured value of the parameter and transmits it to the analytical computation means 140.

The analytical computation means 140 then compares, in a step E30, the numerical data item against the predetermined range of values representative of a functioning of the anti-pollution system in accordance with a predetermined standard.

If the numerical data item is not within the corresponding range of values, the analytical computation means 140, in a step E40, stores the numerical data item in its memory zone so as to record an abnormal functioning of the anti-pollution system.

In the wake of the measurement, at the time of diagnostics on the vehicle 1, an operator connects an analytical terminal 2 to the vehicle 1. The analytical terminal 2 then recovers, in a step E50, the data stored in the memory zone and, in a step E60, displays a signal of detection of an abnormal functioning so as to alert the operator.

When the stored data item is below the lower boundary of the range of values, it is possible to determine that the anti-pollution system has deteriorated.

When the stored data item is above the upper boundary of the range of values, it is possible to determine that the anti-pollution system has been falsified.

Thus, via direct exploitation of the raw (i.e. unprocessed) numerical data sent by the sensor 110, any abnormal functioning of the anti-pollution system, be this due to deterioration or falsification, can be detected.

Furthermore, by virtue of continuous measurement of the parameter, the functioning of the anti-pollution system may be analyzed in real time and an operator can detect an abnormal functioning on the basis of the storage of the data.

The storage of the data only when they are outside their range of values makes it possible to limit the number of data that are stored.

The invention claimed is:

1. A method for analyzing a functioning of an anti-pollution system of a motor vehicle (1) with a combustion engine, said motor vehicle (1) equipped with a measurement sensor (110) that measures a parameter of the motor vehicle (1) and an analytical computation means (140) connected to said measurement sensor (110), said method comprising:
    measuring, by the measurement sensor (110), at least one parameter of the motor vehicle (1);
    generating (E20), by the measurement sensor (110), a numerical data item representative of the measured value of the parameter;
    transmitting, by the measurement sensor (110), said numerical data item to the analytical computation means (140), the transmitting being effected over a direct communication link (L1) between the measurement sensor (110) and the analytical computation means (140);
    comparing (E30), by the analytical computation means (140), said numerical data item against a predetermined range of values defined by an upper boundary and a lower boundary, said predetermined range of values being representative of the functioning of the anti-pollution system in accordance with a predetermined standard; and
    storing (E40) the numerical data item in a memory zone of the analytical computation means only when said numerical data item satisfies any of the following two conditions:
        i) said numerical data item is less than the lower boundary of said predetermined range of values,
        ii) said numerical data item is greater than the higher boundary of said predetermined range of values,
    wherein the stored numerical data item being less than the lower boundary of said predetermined range of values indicates that the anti-pollution system has suffered a deterioration, and the stored numerical data item being greater than the upper boundary of said predetermined range of values indicates that the numerical data item has been falsified.

2. The method as claimed in claim 1, wherein said numerical data item is a data item in hexadecimal format.

3. The method as claimed in claim 2, further comprising:
    acquiring (E50) the numerical data item stored in the memory zone.

4. The method as claimed in claim 2, wherein the parameter of the motor vehicle (1) is measured at a functioning point of the motor vehicle (1), and the predetermined range of values corresponds to said functioning point.

5. The method as claimed in claim 2, further comprising:
    a preliminary step (E0) of determining the predetermined range of values at a functioning point of the motor vehicle (1).

6. The method as claimed in claim 1, further comprising:
acquiring (E50) the numerical data item stored in the memory zone.

7. The method as claimed in claim 6, wherein the numerical data item stored is acquired by an analytical terminal (2) connected to the motor vehicle (1).

8. The method as claimed in claim 7, wherein the parameter of the motor vehicle (1) is measured at a functioning point of the motor vehicle (1), and the predetermined range of values corresponds to said functioning point.

9. The method as claimed in claim 7, further comprising:
a preliminary step (E0) of determining the predetermined range of values at a functioning point of the motor vehicle (1).

10. The method as claimed in claim 6, wherein the parameter of the motor vehicle (1) is measured at a functioning point of the motor vehicle (1), and the predetermined range of values corresponds to said functioning point.

11. The method as claimed in claim 6, further comprising:
a preliminary step (E0) of determining the predetermined range of values at a functioning point of the motor vehicle (1).

12. The method as claimed in claim 1, wherein the parameter of the motor vehicle (1) is measured at a functioning point of the motor vehicle (1), and the predetermined range of values corresponds to said functioning point.

13. The method as claimed in claim 12, wherein the functioning point of the motor vehicle (1) is defined by a speed of rotation of the combustion engine, a speed of the motor vehicle (1), a temperature of the combustion engine and/or a temperature outside of the motor vehicle (1).

14. The method as claimed in claim 13, wherein the memory zone stores a range of values for each of a plurality of functioning points of the combustion engine.

15. The method as claimed in claim 12, further comprising:
a preliminary step (E0) of determining the predetermined range of values at the functioning point of the motor vehicle (1).

16. The method as claimed in claim 1, further comprising:
a preliminary step (E0) of determining the predetermined range of values at a functioning point of the motor vehicle (1).

17. The method as claimed in claim 16, wherein the functioning point of the motor vehicle (1) is defined by a speed of rotation of the combustion engine, a speed of the motor vehicle (1), a temperature of the combustion engine and/or a temperature outside of the motor vehicle (1).

18. A motor vehicle (1), comprising:
a measurement sensor (110) that measures a parameter of the motor vehicle (1), said measurement sensor configured to generate a numerical data item representative of a measured value of the measured parameter; and
analytical computation means (140), connected to said measurement sensor (110) and comprising a memory zone, said measurement sensor directly connected to said analytical computation means (140) via a direct communication link (L1) between the measurement sensor (110) and the analytical computation means (140),
wherein said analytical computation means (140) is adapted to:
receive said numerical data item, transmitted from the measurement sensor (110) via the direct communication link (L1) to the analytical computation means (140);
compare (E30) said numerical data item against a predetermined range of values defined by an upper boundary and a lower boundary, said predetermined range of values being representative of a functioning of an anti-pollution system in accordance with a predetermined standard; and
store (E40) the numerical data item in a memory zone of the analytical computation means only when said numerical data item satisfies any of the following two conditions:
i) said numerical data item is less than the lower boundary of said predetermined range of values,
ii) said numerical data item is greater than the higher boundary of said predetermined range of values,
wherein the stored numerical data item being less than the lower boundary of said predetermined range of values indicates that the anti-pollution system has suffered a deterioration, and the stored numerical data item being greater than the upper boundary of said predetermined range of values indicates that the numerical data item has been falsified.

19. The motor vehicle (1) as claimed in claim 18, wherein the direct communication link (L1) connects the measurement sensor (110) to the analytical computation means (140) with no intermediate component and with no software processing between the measurement sensor and the analytical computation means.

* * * * *